(12) United States Patent
Ryan

(10) Patent No.: US 12,151,077 B2
(45) Date of Patent: Nov. 26, 2024

(54) CONNECTOR CAP

(71) Applicant: Becton, Dickinson and Company, Franklin Lakes, NJ (US)

(72) Inventor: Kevin Ryan, Whitehouse Station, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 577 days.

(21) Appl. No.: 15/957,208

(22) Filed: Apr. 19, 2018

(65) Prior Publication Data

US 2018/0304067 A1  Oct. 25, 2018

Related U.S. Application Data

(60) Provisional application No. 62/488,266, filed on Apr. 21, 2017.

(51) Int. Cl.
*A61M 39/20* (2006.01)
*A61M 39/10* (2006.01)
*A61M 39/16* (2006.01)

(52) U.S. Cl.
CPC ........ *A61M 39/20* (2013.01); *A61M 39/1011* (2013.01); *A61M 39/162* (2013.01);
(Continued)

(58) Field of Classification Search
CPC ................ A61M 39/162; A61M 39/20; A61M 2039/0288; A61M 2039/205;
(Continued)

(56) References Cited

U.S. PATENT DOCUMENTS 3,435,978 A * 4/1969 Wittwer ................. B65D 55/02
411/262
3,650,426 A * 3/1972 Miller .................. B65D 50/041
215/220
(Continued)

FOREIGN PATENT DOCUMENTS

CN  205108731 U   3/2016
JP  H 08-317994 A  12/1996
(Continued)

OTHER PUBLICATIONS

3M Health Care, "3M Curos Jet Disinfecting Cap Video," YouTube, Nov. 21, 2016, 1:12, 1:21-1:34. www.youtube.com/watch?v=MiUNz7lmuK4.

*Primary Examiner* — Kami A Bosworth
(74) *Attorney, Agent, or Firm* — Dickinson Wright PLLC

(57) ABSTRACT

A connector caps that can reduce risk of accidentally removing the cap include a locking feature where outer housing is designed to prevent removal of the cap unless a downward force is applied to the cap with counter clockwise rotation. Structural elements making up the cap locking feature can be optimized or varied, for example to require application of more or less force, more or less downward movement, more or less rotational movement, and variations of other characteristics to facilitate intentional removal and/or to prevent unintentional removal of the cap from the needleless connector, and/or to facilitate securing of the cap on the needleless connector. Optionally, a needleless connector cap can include an outer housing providing holes or openings or vents such that air can pass through if the cap becomes lodged in air passage way.

18 Claims, 10 Drawing Sheets

(52) U.S. Cl.
CPC ............... *A61M 2039/1038* (2013.01); *A61M 2039/205* (2013.01)

(58) Field of Classification Search
CPC .... A61M 2005/3104; A61M 2005/312; A61B 1/00137; A61B 5/150351; A61B 5/150534; A61B 90/70; A61B 2090/701; A61L 2202/18; A61L 2202/182; A61L 2202/23; A61L 2202/24; B65D 50/04; B65D 50/041; B65D 50/043
See application file for complete search history.

(56) References Cited

U.S. PATENT DOCUMENTS

| | | | | |
|---|---|---|---|---|
| 3,843,006 | A * | 10/1974 | Naito | B65D 50/041 |
| | | | | 215/220 |
| 4,697,715 | A * | 10/1987 | Beruvides | B05B 11/1045 |
| | | | | 215/330 |
| 5,292,020 | A * | 3/1994 | Narin | B65D 41/0471 |
| | | | | 215/331 |
| 5,954,957 | A | 9/1999 | Chin-Loy et al. | |
| 6,095,353 | A * | 8/2000 | Gargiulo | B65D 50/041 |
| | | | | 215/277 |
| 8,177,761 | B2 * | 5/2012 | Howlett | A61M 39/20 |
| | | | | 604/905 |
| 2005/0077262 | A1 * | 4/2005 | Bertani | B65D 50/068 |
| | | | | 215/207 |
| 2005/0165351 | A1 | 7/2005 | Tamagni, Jr. | |
| 2007/0112333 | A1 * | 5/2007 | Hoang | A61M 39/20 |
| | | | | 604/533 |
| 2008/0019889 | A1 | 1/2008 | Rogers et al. | |
| 2008/0086091 | A1 * | 4/2008 | Anderson | A61M 39/162 |
| | | | | 604/263 |
| 2008/0147047 | A1 * | 6/2008 | Davis | A61M 39/20 |
| | | | | 604/533 |
| 2009/0028750 | A1 | 1/2009 | Ryan | |
| 2009/0223963 | A1 * | 9/2009 | Bisio | B65D 75/5883 |
| | | | | 220/304 |
| 2011/0015580 | A1 | 1/2011 | Stroup | |
| 2011/0224651 | A1 * | 9/2011 | Ziman | A61M 39/10 |
| | | | | 604/533 |
| 2011/0314619 | A1 | 12/2011 | Schweikert | |
| 2012/0216359 | A1 | 8/2012 | Rogers et al. | |
| 2013/0270270 | A1 | 10/2013 | Reinders | |
| 2014/0188089 | A1 | 7/2014 | Midgette et al. | |
| 2014/0261581 | A1 | 9/2014 | Rogers | |
| 2016/0325089 | A1 | 11/2016 | Burkholz | |

FOREIGN PATENT DOCUMENTS

| | | |
|---|---|---|
| JP | 2004-001901 A | 1/2004 |
| JP | 2014-513569 A | 6/2014 |
| JP | 103990226 A | 8/2014 |
| JP | 2016-511111 A | 4/2016 |
| WO | WO-2008100950 A2 | 8/2008 |
| WO | WO-2010141508 A1 | 12/2010 |
| WO | WO-2011066586 A1 | 6/2011 |

* cited by examiner

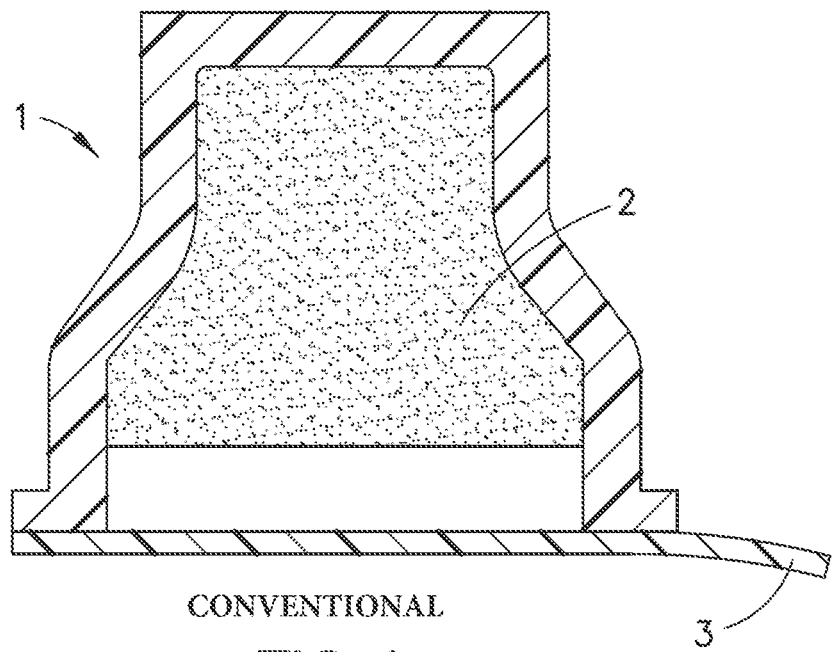
CONVENTIONAL
FIG.1
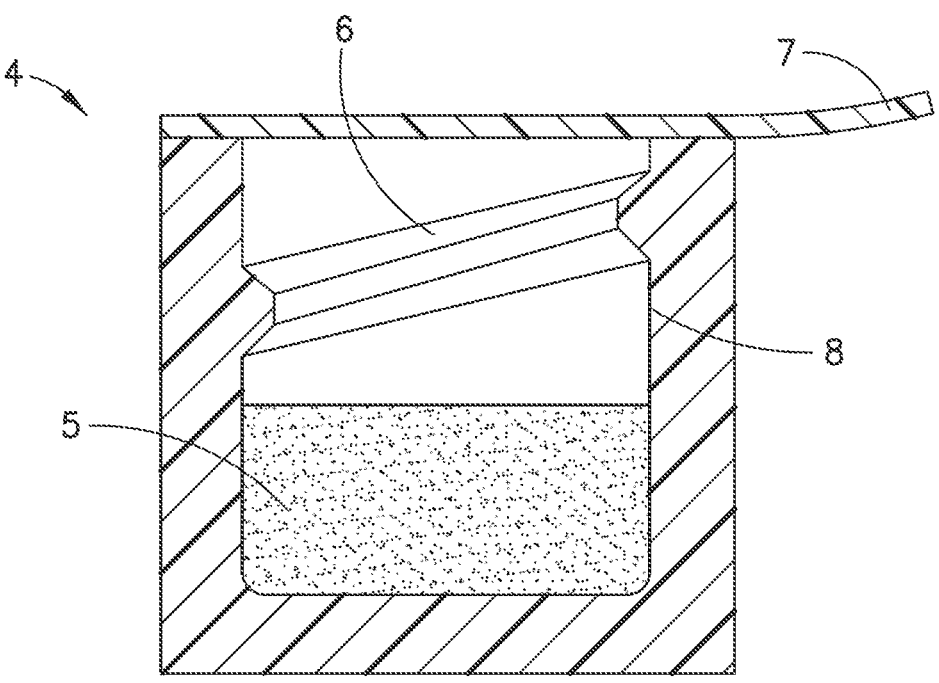
CONVENTIONAL
FIG.2

CONNECTOR CAP

CROSS-REFERENCE TO RELATED APPLICATIONS

This application claim priority under 35 USC § 119(e) from U.S. Provisional Patent Application No. 62/488,266 filed on Apr. 21, 2017, the contents of which (including all attachments filed therewith) are hereby incorporated by reference in their entirety.

TECHNICAL FIELD

Generally, exemplary embodiments of the present disclosure relate to the fields of medical caps, including medical connector caps, and in particular connector caps and/or disinfection caps for uses with IV needleless connectors.

BACKGROUND

In developed markets, when utilizing an IV catheter, a needleless connector will typically be used to close off the system and then subsequently accessed to administer medication or other necessary fluids via the catheter to the patient. Various conventional caps for closing off a needleless connector while not in use have been known for some time. In order to decrease Catheter-related bloodstream infection (CRBSI) cases disinfection caps were originally disclosed in U.S. Patent Publication No. 2007/011233 which issued as U.S. Pat. No. 8,740,864 (the entire disclosures of both of which are incorporated herein by reference), and introduced on the market. Connector caps, including disinfection caps, such as disclosed in the U.S. Pat. No. 8,740,864 are illustrated in FIGS. 1 and 2 herein, where cap 1 includes a disinfecting pad 2 and a lid 3, and cap 4 includes a disinfecting pad 5 and lid 7, as well as threads 6 on its inner circumference 8 to interlock with needleless connector hub. On the other hand, other convention caps may have similar features but exclude the disinfecting pad. Disinfection caps have been added to the Society for Healthcare Epidemiology of America (SHEA) guidelines and early indications are that caps will also be incorporated into the 2016 Infusion Nurses Standards (INS) guidelines.

Further improved designs for connector caps, including disinfection caps, are disclosed in related U.S. patent applications Ser. Nos. 15/408,278 and 15/408,187, both filed on Jan. 17, 2017 (the entire disclosures of both of which are incorporated herein by reference).

Unfortunately, conventional caps, with or without the disinfecting feature, on the market today may pose choking hazard for example due to their relatively small size and ease of removal from a needles connector. Consequently, needleless connector caps are typically not used in situations where they may be inadvertently removed, for example by a child, causing potential safety concerns. At this time, there is no needleless connector cap device on the market that addresses such potential safety concerns, for example by locking the cap to prevent inadvertent removal of the cap from a needleless connector.

Hence there is a need for a safety locking integration with needleless connector caps.

SUMMARY

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

As would be readily appreciated by skilled artisans in the relevant art, while descriptive terms such as "lock", "hole", "tip", "hub", "thread", "sponge", "protrusion", "slope", "wall", "top", "side" and others are used throughout this specification to facilitate understanding, it is not intended to limit any components that can be used in combinations or individually to implement various aspects of the embodiments of the present disclosure.

Exemplary embodiments of the disclosure provide connector caps that can reduce the risk of accidentally (or, for example, by a child) removing the cap by including a locking feature. Optionally, in any exemplary implementation of the disclosed embodiments, a needleless connector cap includes an outer housing that is designed to prevent removal of the cap unless a downward force is applied to the cap with counter clockwise rotation.

Optionally, according to further exemplary implementations of any of the disclosed embodiments, configuration of structural elements making up the cap locking feature can be optimized or varied, for example to require application of more or less force, more or less downward movement, more or less rotational movement, and variations of other characteristics to facilitate intentional removal and/or to prevent unintentional removal of the cap from the needleless connector, and/or to facilitate securing of the cap on the needleless connector.

Optionally, according to yet further exemplary implementations of any of the disclosed embodiments, a connector cap includes an outer housing that is further designed to provide holes or openings or vents such that air can pass through if the cap becomes lodged in air passage way.

Optionally, according to yet further exemplary implementations of the disclosed embodiments, a connector cap comprises: an inner housing comprising a first top wall, an essentially cylindrical first sidewall, an open bottom formed by said first sidewall with an opening to an inner cavity within said inner housing for receiving a hub of a needleless connector, and at least one cap thread on an inner sidewall surface of said first sidewall, said cap thread being sufficient to interlock with a mating feature of said hub of said needleless connector; an outer housing comprising a second top wall configured above said first top wall, and an essentially cylindrical second side wall configured to essentially surround said first sidewall; and a safety interface comprising a first portion configured on an outer surface of said first top wall, and a second portion configured on an inner surface of said second top wall. The safety interface transfers a rotational movement of said outer housing to a rotational movement of said inner housing in the same rotational direction when said first top wall and said second top wall are urged toward each other and said first portion and said second portion engage.

Optionally, according to yet further exemplary implementations of the disclosed embodiments, the first portion of said safety interface comprising at least one first protrusion, and the second portion of said safety interface comprises at least one second protrusion.

Optionally, according to yet further exemplary implementations of the disclosed embodiments, at least one of said first protrusion and said second protrusion comprises a slope surface and a vertical surface.

Optionally, according to yet further exemplary implementations of the disclosed embodiments, said first protrusion comprises a first vertical surface essentially perpendicular to said outer surface of said first top wall and a first slope surface at an acute angle to said outer surface of said first top wall, and said second protrusion comprises a second vertical surface essentially perpendicular to said inner surface of said second top wall and a second slope surface at an acute angle to said inner surface of said second top wall.

Optionally, according to yet further exemplary implementations of the disclosed embodiments, said inner housing comprises an inner housing retaining feature, and said outer housing comprises an outer housing retaining feature, said inner housing retaining feature and said outer housing retaining feature are configured to engage to secure said outer housing on said inner housing and allow rotational movement of said outer housing with respect to said inner housing when said first portion of said safety interface and said second portion of said safety interface are not engaged.

Optionally, according to yet further exemplary implementations of the disclosed embodiments, said inner housing retaining feature comprises a protrusion on an outer surface of said first sidewall of said inner housing, and said outer housing retaining feature comprises a recess in an inner surface of said second sidewall of said outer housing, said protrusion and said recess are configured to engage to secure said outer housing on said inner housing.

Optionally, according to yet further exemplary implementations of the disclosed embodiments, said inner housing retaining feature comprises a first latching protrusion on an outer surface of said first top wall of said inner housing, and said outer housing retaining feature comprises a second latching protrusion on an inner surface of said second top wall of said outer housing, said first latching protrusion and said second latching protrusion are configured to latch to secure said outer housing on said inner housing.

Optionally, according to yet further exemplary implementations of the disclosed embodiments, said second top wall of said outer housing comprises at least one opening extending through said top wall allowing air to pass through said outer housing.

Optionally, according to yet further exemplary implementations of the disclosed embodiments, said inner housing and said outer housing are configured to allow said air passing through said at least one opening to pass between an inner surface of said outer housing and an outer surface of said inner housing.

Optionally, according to yet further exemplary implementations of the disclosed embodiments, an application of a rotational force to said outer housing causes said rotational movement of said outer housing, and said second portion of said safety interface to engage said first portion of said safety interface to transfer said rotational movement of said outer housing to said rotational movement of said inner housing to threadably rotate said inner housing to interlock said cap thread with said mating feature of said hub of said needleless connector.

Optionally, according to yet further exemplary implementations of the disclosed embodiments, application of an axial force to said outer housing in a direction of said inner housing facilitates said second portion of said safety interface to engage that first portion of said safety interface.

Optionally, according to yet further exemplary implementations of the disclosed embodiments, continuous application of an axial force to said outer housing in a direction of said inner housing causes said second portion of said safety interface to engage that first portion of said safety interface in an interference fit, and application of a rotational force to said outer housing causes said rotational movement of said outer housing, and said second portion of said safety interface to continue to engage said first portion of said safety interface to transfer said rotational movement of said outer housing to said rotational movement of said inner housing to threadably rotate said inner housing to remove said cap thread from said mating feature of said hub of said needleless connector.

Optionally, according to yet further exemplary implementations of the disclosed embodiments, a disinfection sponge can be configured within said inner cavity, and a removable cover can be provided sealing said opening to said inner cavity to seal said sponge within said inner cavity prior to use of said cap.

Optionally, according to yet further exemplary implementations of the disclosed embodiments, the cap thread does not correspond to the mating feature of the needleless connector.

Optionally, according to yet further exemplary implementations of the disclosed embodiments, at least one of a major diameter, a minor diameter, a pitch, a thread section profile, and a number of threads of said cap thread does not correspond to said mating feature of said hub.

Optionally, according to yet further exemplary implementations of the disclosed embodiments, at least one cap thread on said inner sidewall surface of said sidewall comprises a protrusion formed on a least a portion of said cap thread to facilitate said interlocking with said mating feature of said needleless connector.

Optionally, according to yet further exemplary implementations of the disclosed embodiments, at least a portion of said at least one cap thread comprises a non-engaging portion that does not engage said mating feature of said needleless connector.

Optionally, according to yet further exemplary implementations of the disclosed embodiments, said cap thread comprises at least one interlocking portion formed on a least a portion of said cap thread to facilitate said interlocking with said mating feature of said needleless connector, and at least one non-engaging portions that does not engage said mating feature of said needleless connector.

Optionally, according to yet further exemplary implementations of the disclosed embodiments, the cap thread comprises a first start thread path wherein the first start thread path has a major profile, a minor profile, a pitch, and a first thread section profile, at least a second start thread path wherein the second start thread path has a major profile, a minor profile, a pitch, and a second thread section profile, where the first thread section profile and the second thread section profile are different.

Objects, advantages, and salient features of the disclosure will become apparent from the following detailed description, which, taken in conjunction with the annexed drawings, discloses exemplary embodiments of the disclosure.

BRIEF DESCRIPTION OF THE DRAWINGS

Referring now to the drawings, wherein like reference numerals designate identical or corresponding parts throughout the several views, embodiments of the present disclosure are described as follows.

FIGS. 1 and 2 are cross sectional views of conventional caps for needleless connectors.

Throughout the drawings, like reference numbers will be understood to refer to like parts, components and structures.

DETAILED DESCRIPTION OF THE EXEMPLARY EMBODIMENTS

Figure 3A:
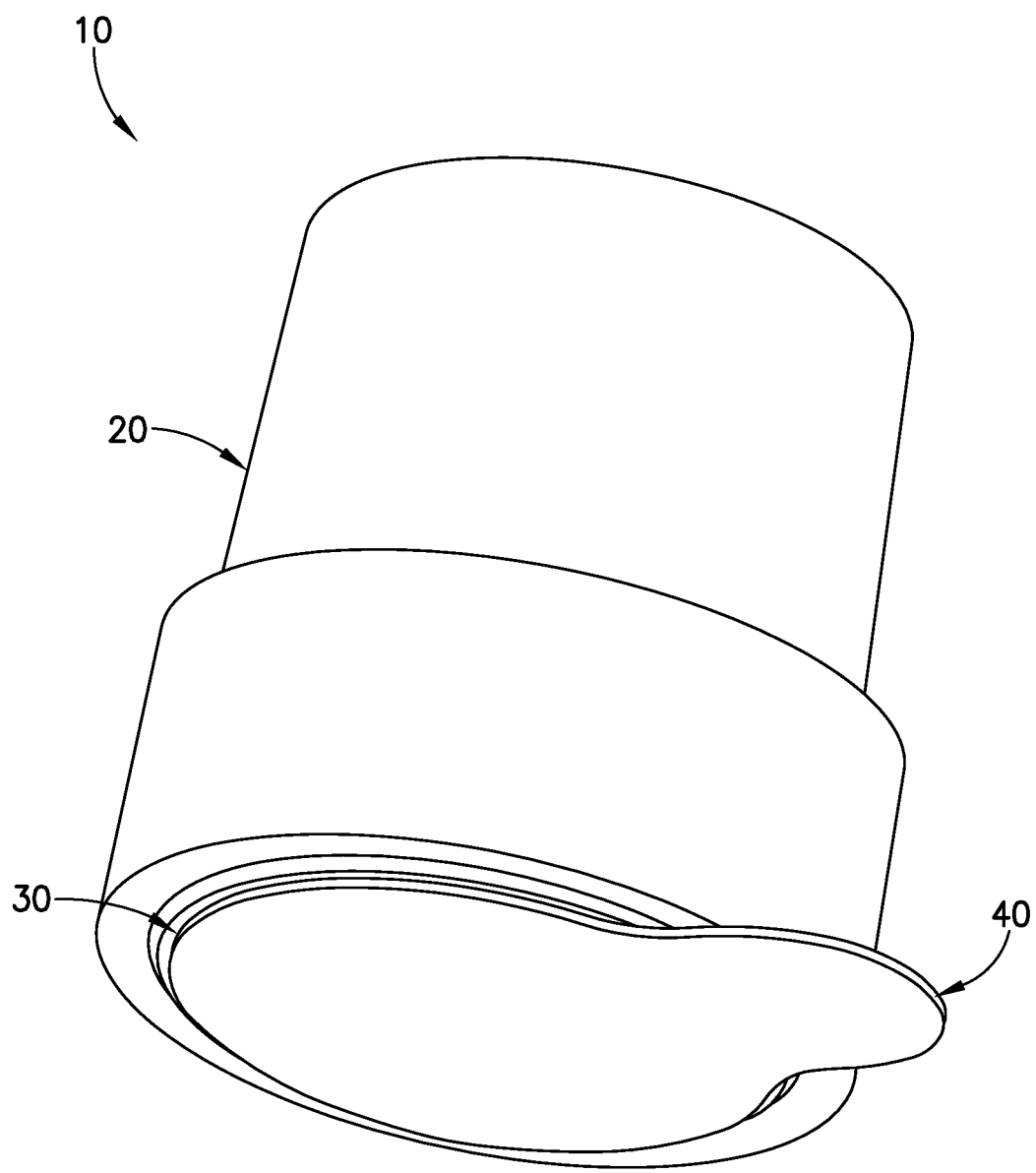
FIG. 3A is a three-dimensional views of a cap according to an exemplary embodiment of the present disclosure.

This matters exemplified in this description are provided to assist with a comprehensive understanding of exemplary embodiments with reference to the accompanying drawing figures. Accordingly, those of ordinary skill in the art will recognize that various changes and modifications of the exemplary embodiments described herein can be made within the scope of appended claims without departing from their full scope and equivalents. Also, descriptions of well-known functions and constructions are omitted for clarity and conciseness. Likewise, certain naming conventions, labels and terms as used in the context of the present disclosure are non-limiting and provided only for illustrative purposes to facilitate understanding of exemplary implementations of the exemplary embodiments Referring to FIGS. 3A-6, according to exemplary embodiments of the present disclosure a safety locking connector cap 10 comprises an outer housing 20 which includes a top wall 22 and a sidewall 26, an inner housing 30 which includes a top wall 32 and a sidewall 36 with an opening 37 into inner cavity 38 and one or more threads 31 on inner sidewall surface 33 of sidewall 36, a peel sealing film 40 which seals opening, a disinfecting member 50, such as an IPA soaked sponge, and a sealing surface 60, which can be constituted by a surface of a rim of an open bottom of inner housing 30.

Cavity 38 of inner housing 30 receives a tip of a needleless connector 9 after the peel sealing film 40 is removed or when the peal sealing film is pierced, and threadably secures the tip of needleless connector 9 within cavity 38, one or more threads 31 being sufficient to interlock with a mating feature of a hub or tip of needleless connector 9 as described for example in related U.S. patent applications Ser. Nos. 15/408,278 and 15/408,187, both filed on Jan. 17, 2017.

Figure 3B:
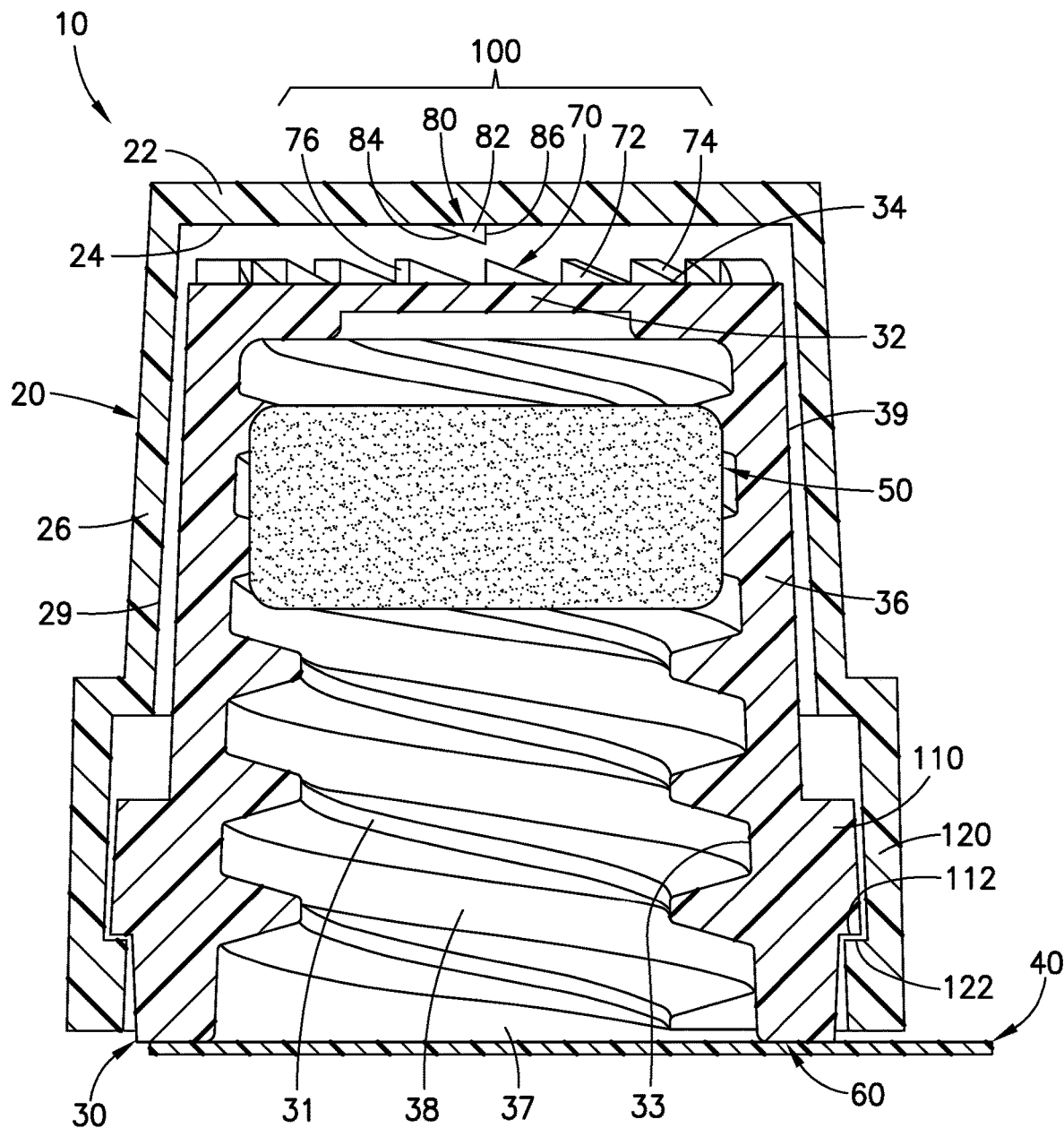
FIG. 3B is a cross sectional view of a cap according to an exemplary embodiment of the present disclosure.

Referring for example to FIGS. 3A and 3B, in an exemplary implementations of the embodiments of the present disclosure, inner housing 30 is disposed within outer housing 20 such that sidewall 26 essentially surrounds sidewall 36, and top wall 22 essentially covers top wall 32. A safety interface 100 comprises a first portion 70 that can be configured on an outer surface 34 of top wall 32 of inner housing 30 as a ratchet feature comprising one or more protrusions 72 such as a tooth or teeth having a first slope surface 74 and a first vertical surface 76, and a second portion 80 that can be configured on an inner surface 24 of top 22 of outer housing 20 as a ratchet feature comprising one or more protrusions 82 such as a tooth or teeth having a second slope surface 84 and a second vertical surface 86. The first vertical surface 76 can be essentially perpendicular to the outer surface 34, and the first slope surface 74 can be at an acute angle to the outer surface 34. On the other hand, the second vertical surface 86 can be essentially perpendicular to the inner surface 24, and the second slope surface 84 can be at an acute angle to the inner surface 24.

Safety interface 100 is configured such that first portion 70 and second portion 80 do not engage unless the outer surface 34 is sufficiently near the inner surface 24 such that protrusions 72 and 82 can make sufficient contact.

According to a further exemplary implementation of the embodiments of the present disclosure as illustrated in the example of FIG. 3B, a retaining interface to secure outer housing 20 with respect to inner housing 30 can be implemented for example as follows. An outer surface 39 of sidewall 36 of inner housing 30 can include an inner housing retaining feature such as a protrusion (or a skirt, or a flange) 110, and an inner surface 29 of sidewall 26 of outer housing 20 can include an outer housing retaining feature such as a recess 120. Protrusion 110 and recess 120 are configured to engage, for example at respective first contact surface 112 of protrusion 110 and second contact surface 122 of recess 120, such that outer housing 20 is secured on inner housing 30 while allowing rotational movement of outer hosing 20 with respect to inner housing 30, as illustrated for example with reference to examples of FIGS. 5 and 6.

Retaining interface secures outer housing 20 with respect to inner housing 30 while allowing sufficient axial movement of the outer surface 34 with respect to the inner surface 24 such that on the one hand protrusions 72 and 82 do not necessarily contact each other when outer housing 20 is rotated with respect to inner housing 30, and on the other hand protrusions 72 and 82 make sufficient contact with each other to transfer rotational movement of outer housing 20 to inner housing 30.

Figure 3C:
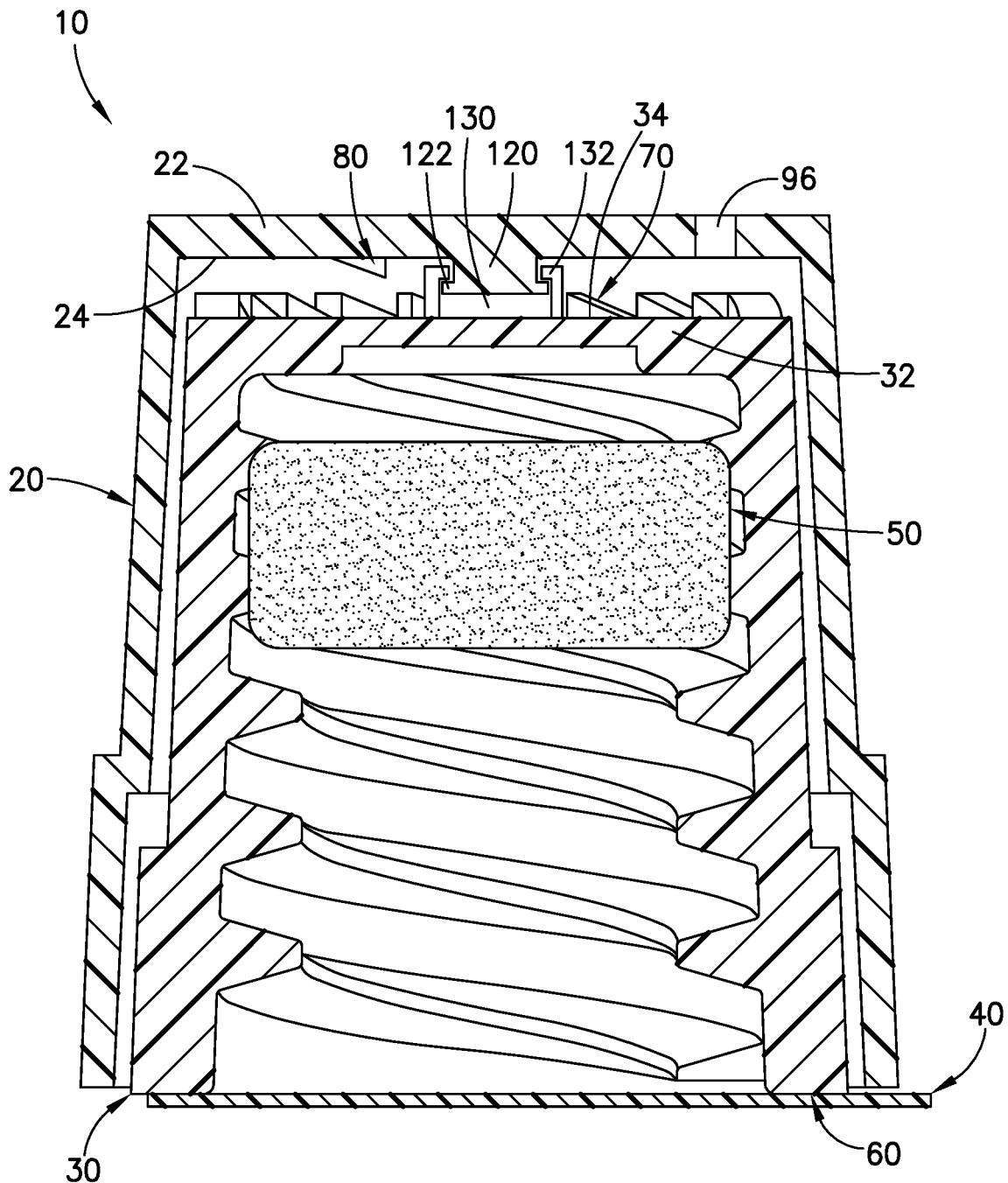
FIG. 3C is a cross sectional view of a cap according to another exemplary embodiment of the present disclosure.

According to another further exemplary implementation of the embodiments of the present disclosure as illustrated in detail in the example of FIG. 3C, a retaining interface to secure outer housing 20 with respect to inner housing 30 can be optionally implemented in addition to, or instead of, the retaining interface shown in FIG. 3B, for example as follows. An outer surface 34 of top wall 32 of inner housing 30 can include an inner housing retaining feature such as a latching protrusion 130, and an inner surface 24 of top wall 22 of outer housing 20 can include an outer housing retaining feature such as a corresponding latching protrusion 120. Protrusion 130 and protrusion 120 are configured to engage, for example by retaining rim 132 of protrusion 130 latching an extended skirt 122 of protrusion 120, such that outer housing 20 is secured on inner housing 30 while allowing rotational movement of outer hosing 20 with respect to inner housing 30, as illustrated below with reference to examples of FIGS. 5 and 6.

Figure 4A:
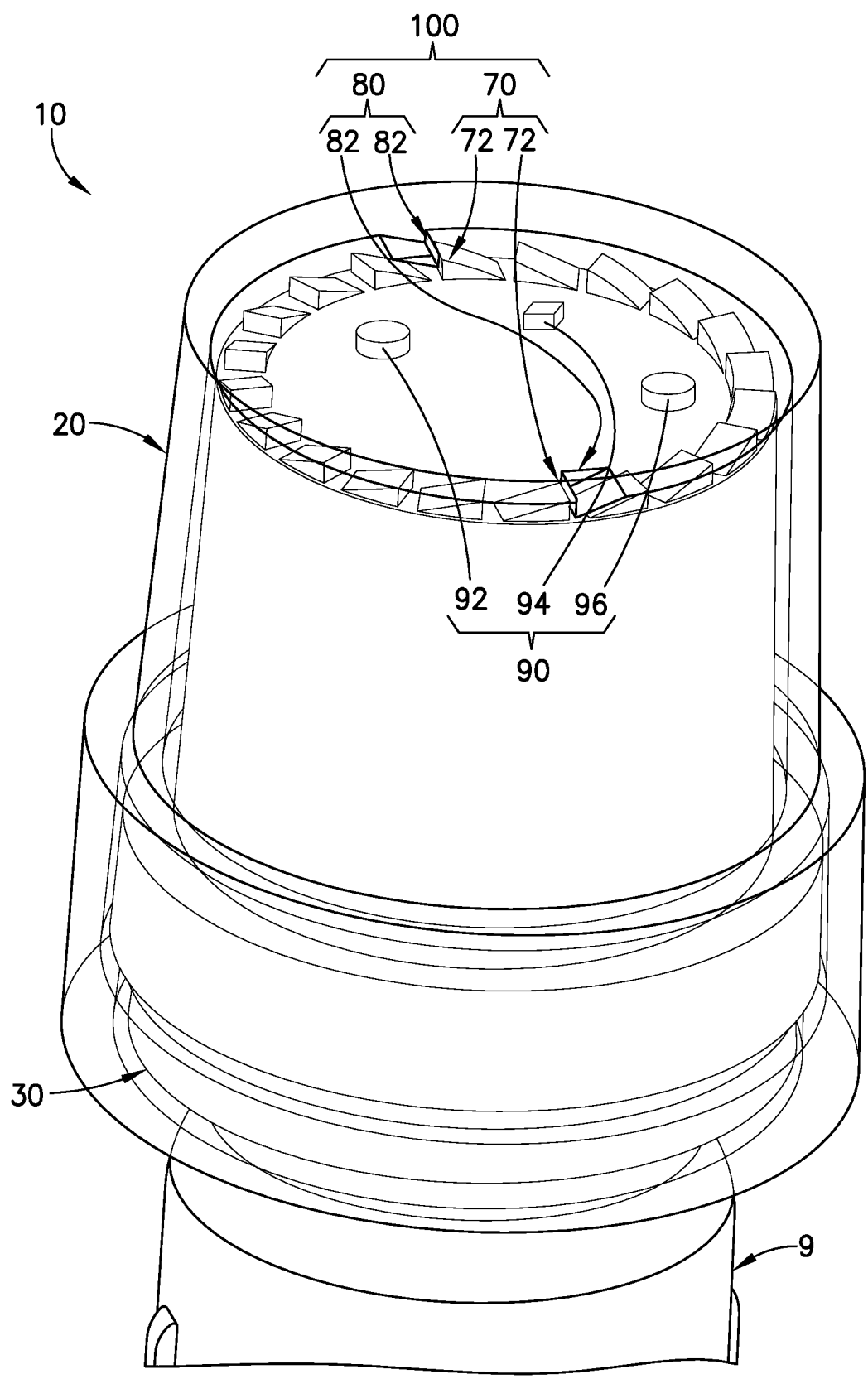
FIG. 4A is a three-dimensional views of a cap according to yet another exemplary embodiment of the present disclosure disposed on a medical implement such as a needleless connector.
Figure 4B:
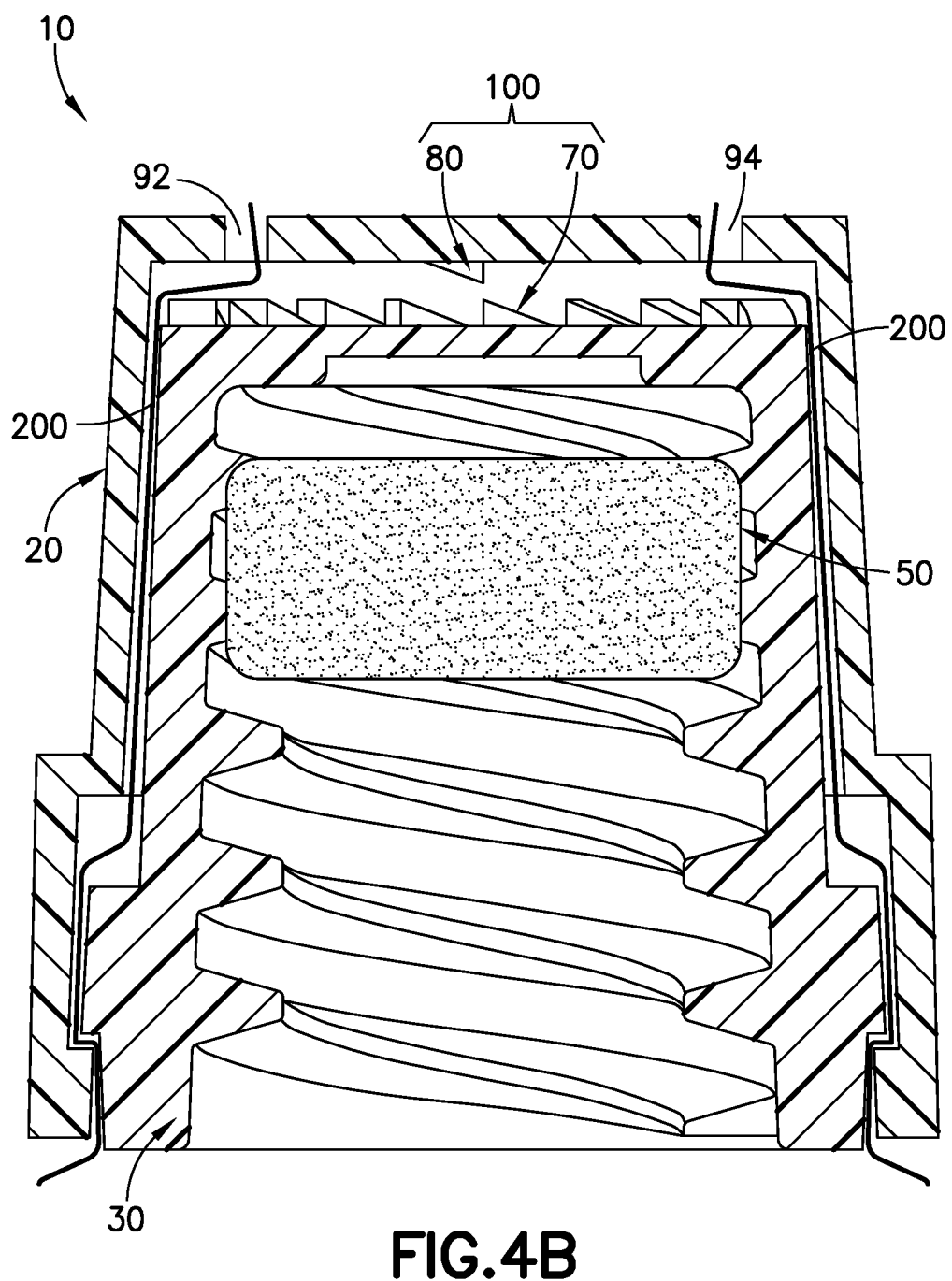
FIG. 4B is an illustration showing a cross-sectional view of a cap according to an exemplary embodiment of the present disclosure.
Figure 4C:
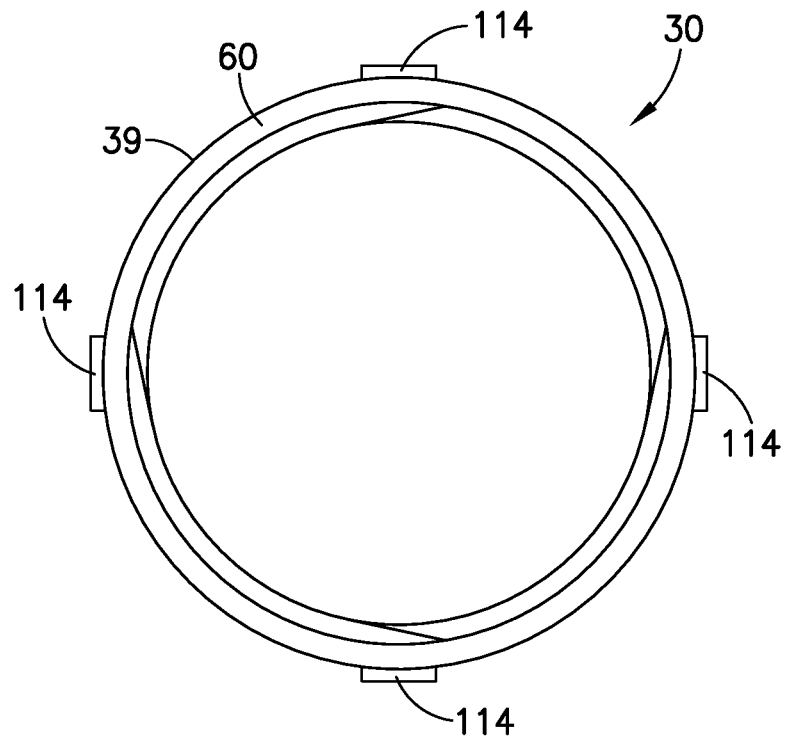
FIG. 4C is an illustration showing a cross-sectional bottom view of a housing according to an exemplary embodiment of the present disclosure.

Referring for example to FIG. 4A-4C, according to exemplary embodiments of the present disclosure, outer housing of a safety locking connector cap 10 is further designed to prevent a choking hazard by providing holes or openings such that air can pass through if the cap becomes lodged in an airway passage, for example a human throat.

As illustrated in the examples of FIGS. 4A and 4B, any exemplary implementations of the embodiments of the present disclosure can optionally provide one or more openings 90, such as openings 92, 94, and/or 96, in top wall 22 of outer housing 20, which allows air 200 to pass through the outer housing 20 for example between the inner surface of outer housing 20 and outer surface of inner housing 30 as diagrammatically illustrated in the example of FIG. 4B. The number, size and/or shape of the openings 92, 94 and/or 96 can vary to ensure sufficient air passage, for example to meet safety concerns, as well as to avoid interference with the operation and/or functionality of the safety interface 100.

Figure 4D:
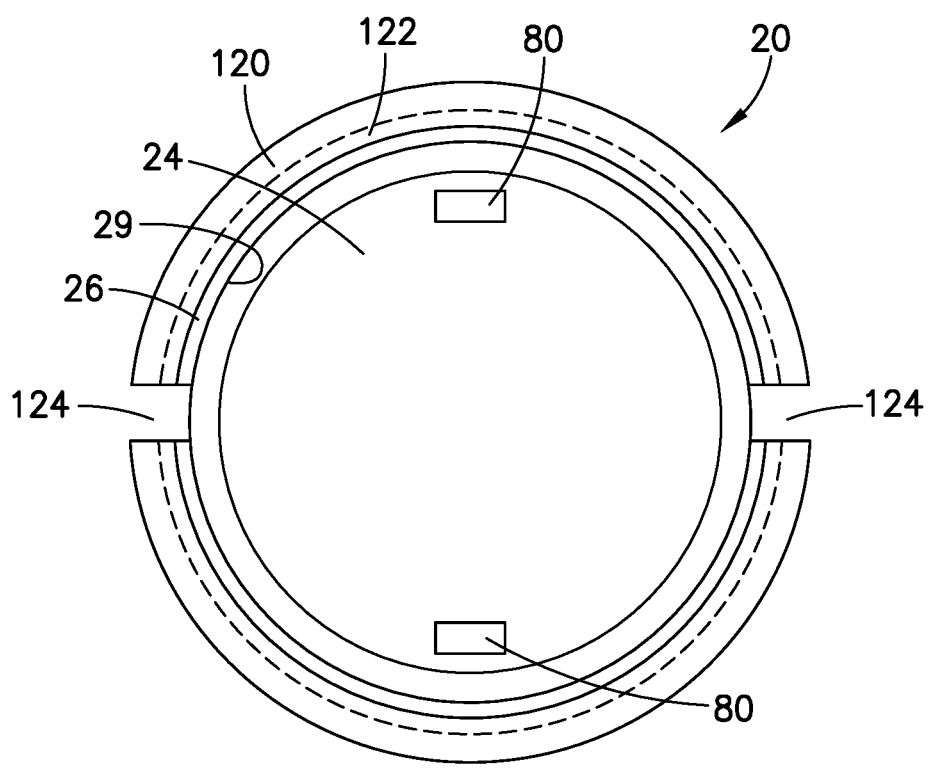
FIG. 4D is an illustration showing a cross-sectional bottom view of a housing according to another exemplary embodiment of the present disclosure.

While the example of FIGS. 3A and 4A diagrammatically illustrates an implementation where both protrusion 110 and recess 120 are optionally formed as continuous 360-degree features of respective inner housing 30 and outer housing 20, according to exemplary embodiments of the present disclosure at least one or both of the protrusion 110 and recess 120 can be optionally formed as partial features. For example as illustrated in FIG. 4C by a cross-sectional bottom view of inner housing 30, instead of a continuous 360-degree feature, protrusion 110 can comprise multiple protruding 10-degree portions 114 centered at 90 degree intervals on outer surface 39 of sidewall 36. On the other hand, for example, instead of a continuous 360-degree feature, recess 120 can have one more gaps 124 as illustrated in FIG. 4D by a cross-sectional bottom view of outer housing 20, which can also facilitates further prevention of a choking hazard by providing air passage if the cap becomes lodged in an airway passage. When forming at least one or both of the protrusion 110 and recess 120 as partial features, sizes and/or shapes of portion 114 and/or gaps 124 can be varied as appropriate and/or desired while ensuring outer housing 20 is properly configured with respect to inner housing 30 to ensure proper operation and/or functionality of the safety interface 100.

Figure 5:
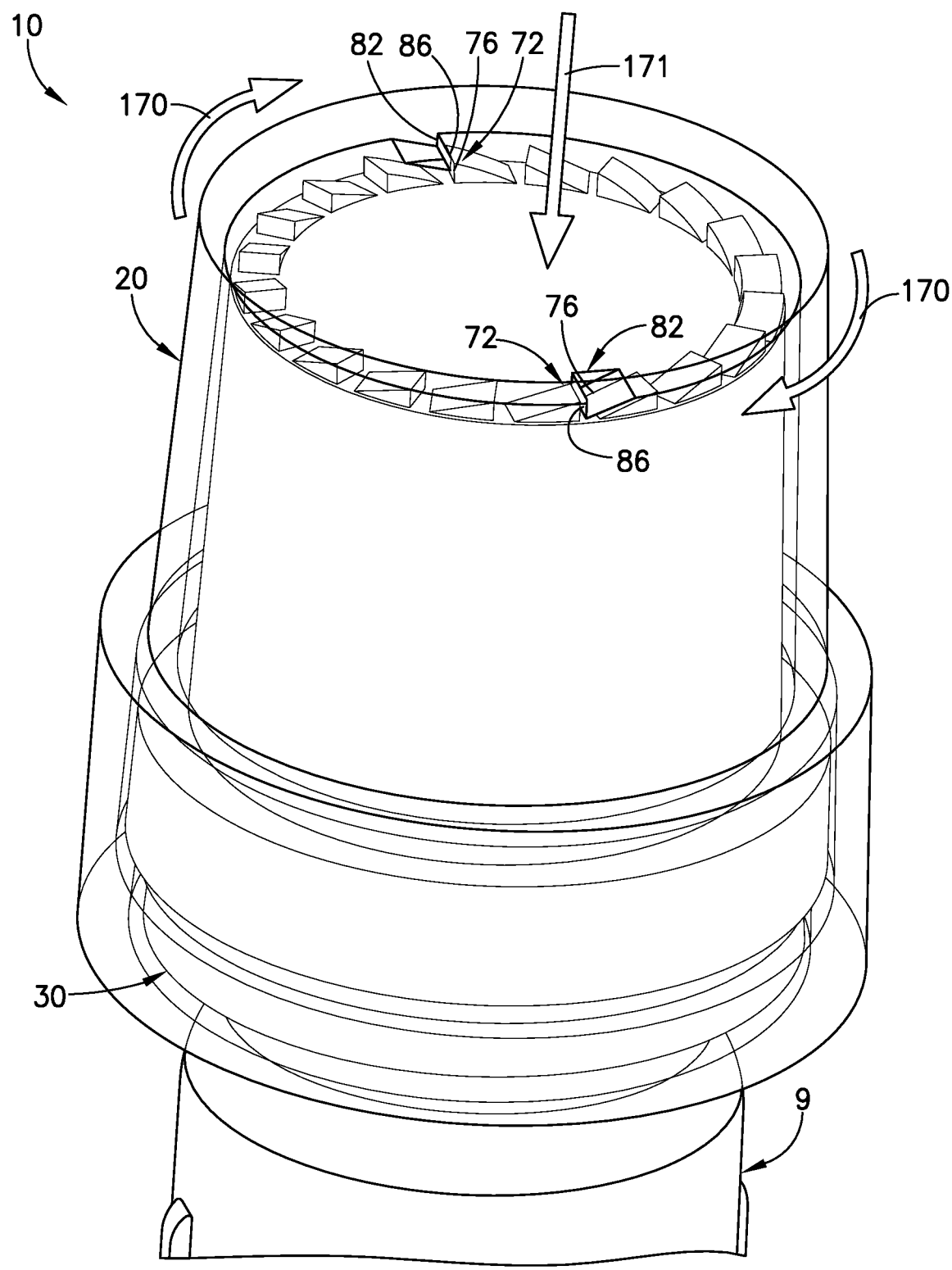
FIGS. 5 and 6 are illustrations diagrammatically showing securing and removing of a cap according to exemplary embodiments of the present disclosure onto and from a medical implement such as a needleless connector.
Figure 6:
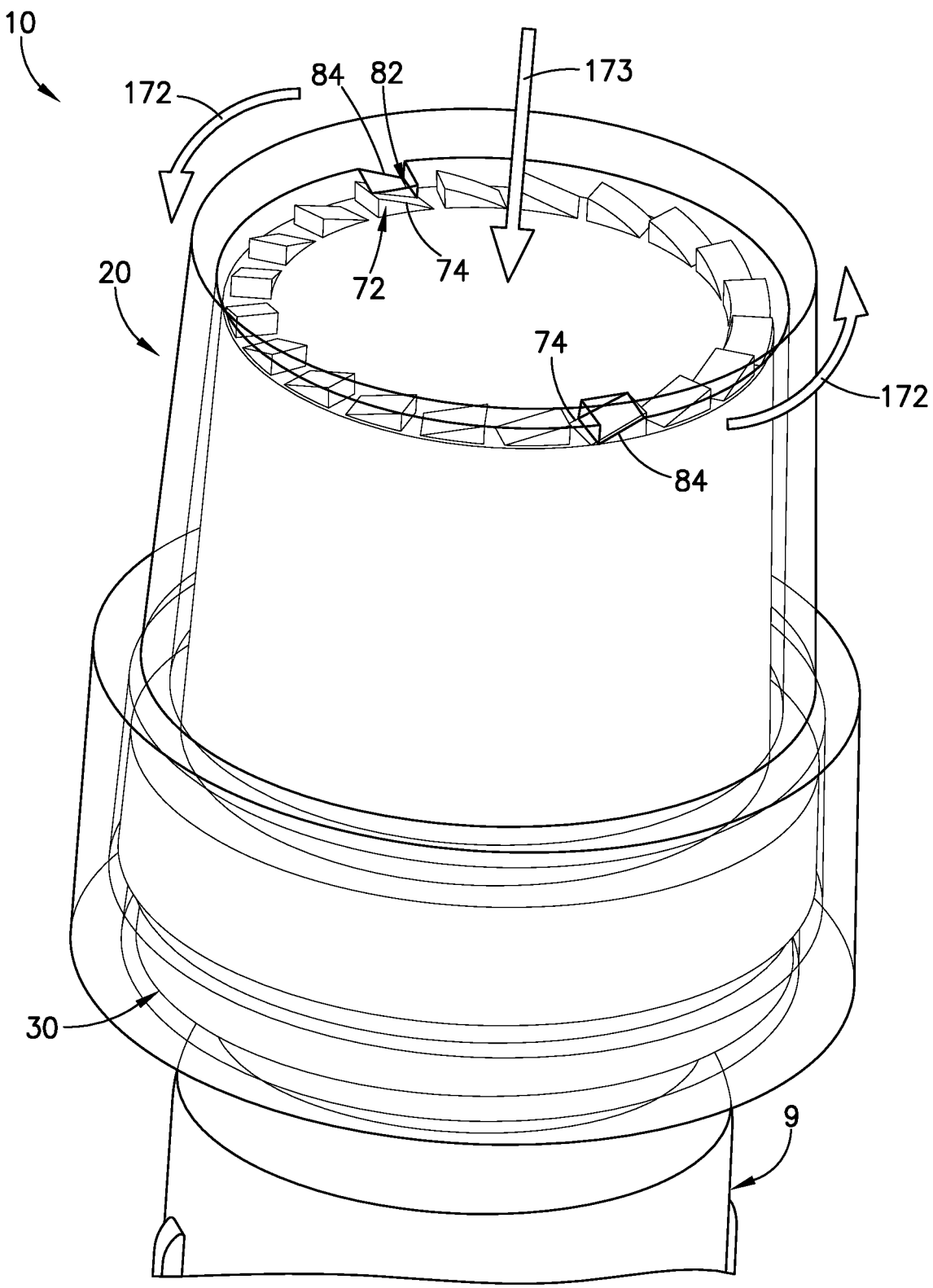

Referring to FIGS. 5 and 6, according to exemplary implementations of the embodiments of the present disclosure, securing cap 10 onto a needleless connector 9 is illustrated in FIG. 5 diagrammatically showing application of axial force 171 causing axial movement of top 22 of outer housing 20 toward top 32 of inner housing 30 and a rotational force 170 causing rotational movement (for example, in a clock-wise direction as may be required to threadably secure cap 10 onto needleless connector 9) of outer housing 20. The axial movement of top 22 toward top 32 reduces the distance between first portion 70 and second portion 80 of safety interface 100 allowing first portion 70 and second portion 80 to engage upon application of rotational force 170. On the other hand, removing cap 10 from a needless connector 9 is illustrated in FIG. 6 diagrammatically showing application of axial force 173 causing axial movement of top 22 of outer housing 20 toward top 32 of inner housing 30 and a rotational force 172 causing rotational movement (for example, in a counter clock-wise direction as maybe required to remove a threadably-secured cap 10 from needleless connector 9) of outer housing 20.

As illustrated in the example of FIG. 5, according to an exemplary implementation of the embodiments of the present disclosure, application of force 171 with force 170 causes one or more first protrusions 72 having a first vertical surface 76 and respective one or more second protrusions 82 having a second vertical surface 86 to engage when oppositely facing essentially vertical surfaces 76 and 86 make contact, resulting in a transfer of the rotation of outer housing 20 to inner housing 30 such that inner housing 30 rotates in the same rotational direction as outer housing 20 to threadably rotate the inner housing onto needleless connector 9 to interlock cap thread 31 with any mating feature of the hub or tip of needleless connector 9 to secure cap 10 onto needleless connector 9.

As illustrated in the example of FIG. 6, according to an exemplary implementation of the embodiments of the present disclosure, continuous application of force 173 with force 172 causes one or more first protrusions 72 having a first surface 74 and respective one or more second protrusions 82 having a second surface 84 to engage when oppositely facing surfaces 74 and 84 make contact resulting in a transfer of the rotation of outer housing 20 to inner housing 30 such that inner housing 30 rotates in the same rotational direction as outer housing 20 to threadably rotate off of needleless connector 9 to release thread 31 from any mating feature of the tip or hub of needleless connector 9 to thereby remove cap 10 from needleless connector 9.

According to an exemplary implementation, force 171 may not need to be applied as an external force (or applied as a force of a relatively small magnitude) since free axial movement of outer housing 20 with respect to inner housing 30 may result in outer housing 20 moving toward inner housing 30 simply due to gravity based on positions of cap 10 with respect to needleless connector 9. On the other hand, force 173 may need to be applied as an external force of a relatively greater magnitude to ensure engagement of one or more of first protrusions 72 with one or more respective second protrusions 82 by, for example, interference fit of respective surfaces 74 and 84. For example, the slope and shape of respective surfaces 74 and 84 can be varied to adjust the amount of axial force 173 required to create sufficient interference fit of respective surfaces 74 and 84 such that protrusions 72 and 82 do not slip with respect to each other but engage to transfer the rotation of outer housing 20 to inner housing 30. For example, an enhanced safety can be optionally achieved by increasing amount of axial force required to engage first portion 70 and second portion 80 in order to threadably rotate inner housing 30 off of needleless connector 9 to remove cap 10 from needleless connector 9.

According to exemplary implementations of the embodiments of the present disclosure, outer housing 30 having the safety features described above with reference to FIGS. 3-6 can be optionally implements with any and all of the disinfectant caps having various features and designs described in Applicant's co-pending US patent applications Nos. U.S. patent applications Ser. Nos. 15/408,278 and 15/408,187, both filed on Jan, 17, 2017, for example by modifying outer surface of the housings of the disinfectant caps disclosed therein as shown in an illustrative example of FIGS. 7A and 7B.

Figure 7A:
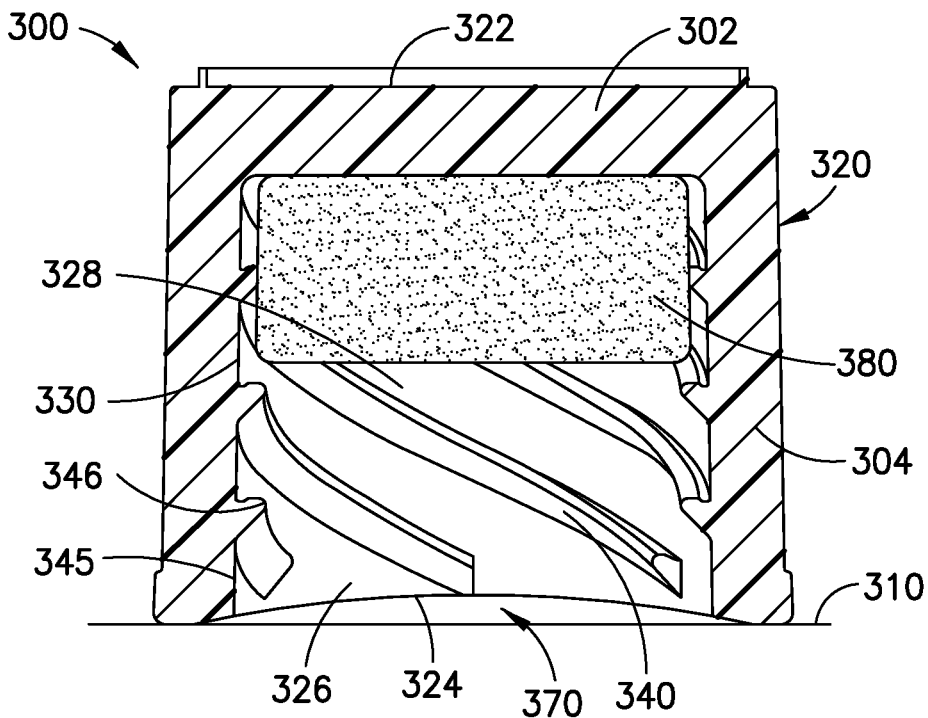
FIG. 7A is a cross-sectional view of a cap according to yet another exemplary embodiment of the present disclosure.
Figure 7B:
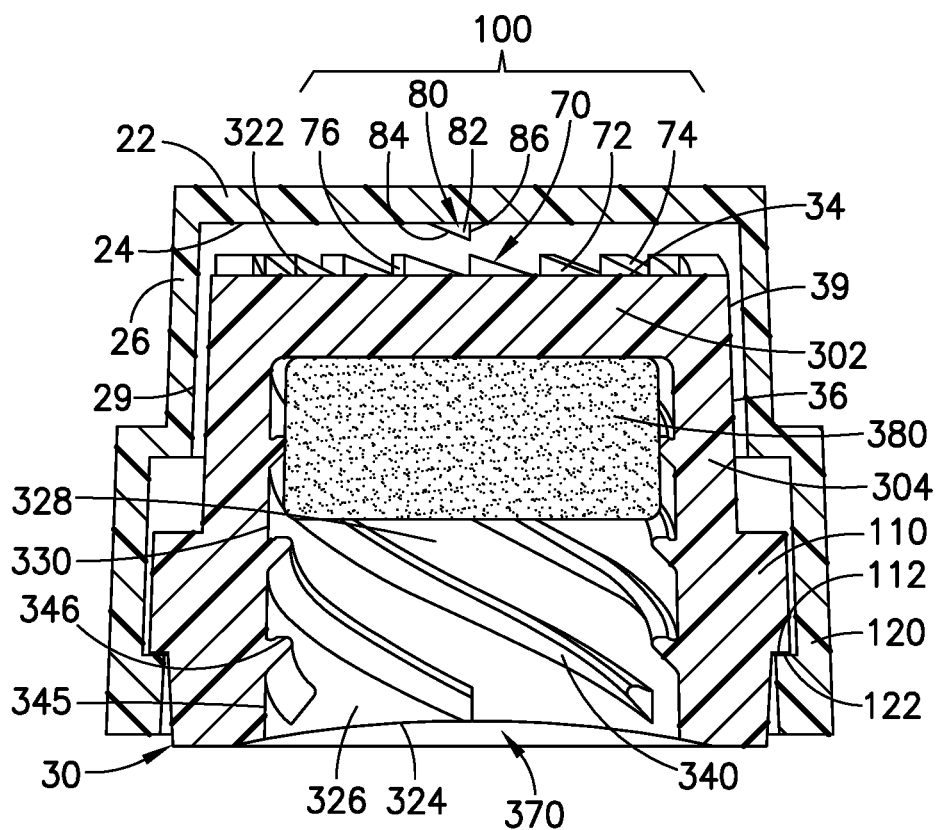
FIG. 7B is a cross-sectional view of a cap according to yet another exemplary embodiment of the present disclosure.

Referring to FIGS. 7A and 7B, a cross thread disinfecting cap 300 has housing 302 comprising: a closed top 322; an essentially cylindrical sidewall 304 with an outer sidewall surface 320; and an open bottom 324 with an opening 326 to an inner cavity 328 within housing 302 for receiving tip of a needleless connector. The bottom 324 formed by sidewall 304 of housing 302 is not flat such that space 370 exists between a flat surface 310 and bottom 324 of cap 300. The inner cavity 328 can accommodate an alcohol soaked disinfection sponge 380 and has threads 340 on inner sidewall surface 330 of sidewall 304. The diameter (major diameter 345 and/or minor diameter 346) of threads 340 of the cap 300 may not correspond to the thread of a needleless connector. According to exemplary implementation of the present disclosure, outer sidewall surface 320 of housing 302 can be modified to include a protrusion 110, as a continuous 360-degree features or as one or more protrusions 114, and outer surface 34 of top 322 can be modified to include one or more second protrusions 72. An outer housing 20 can be shaped and configured with respect to sidewall 320 and top 322 of what becomes an inner housing 30 to form a safety interface 100 as illustrated in the examples of FIGS. 3-6.

While the present disclosure has been shown and described with reference to certain exemplary embodiments thereof, it will be understood by those skilled in the art that various changes in form and details may be made therein without departing from the spirit and scope of the embodiments of the present disclosure. For example, a disinfection sponge can comprise any suitable disinfecting or other application-specific substance, and can be made of any suitable material. Also, the inner and/or the outer housing of the cap can be single shot molded, or made by other suitable process. Furthermore, any of the features or elements of any exemplary implementations of the embodiments of the present disclosure as describes above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of disclosure.

Other objects, advantages and salient features of the disclosure will become apparent to those skilled in the art from the details provided, which, taken in conjunction with the annexed drawing figures, disclose exemplary embodiments of the disclosure.

I claim:

1. A connector cap comprising:
an inner housing comprising
a first top wall,
an essentially cylindrical first sidewall, said first top wall and said first sidewall forming an inner cavity within said inner housing, said first top wall forming a closed top of said inner cavity;
an open bottom formed by said first sidewall with an opening to said inner cavity within said inner housing for receiving a hub of a needleless connector, and
at least one cap thread on an inner sidewall surface of said first sidewall, said at least one cap thread being sufficient to interlock with a mating feature of said hub of said needleless connector;
an outer housing comprising
a second top wall configured above said first top wall, and
an essentially cylindrical second side wall configured to essentially surround said first sidewall;
a safety interface comprising
a first portion formed on an outer surface of said first top wall, and
a second portion formed on an inner surface of said second top wall;
a disinfection sponge configured within said inner cavity; and
a removable cover sealing said opening to said inner cavity to seal said sponge within said inner cavity prior to use of said cap,
wherein said safety interface transfers a rotational movement of said outer housing to a rotational movement of said inner housing in a same rotational direction only when said outer housing including said second sidewall and said inner housing including said first side wall are axially displaced with respect to each other such that said first top wall and said second top wall are urged toward each other and said first portion and said second portion engage.

2. The connector cap of claim 1 wherein:
said first portion of said safety interface comprising at least one first protrusion, and
said second portion of said safety interface comprises at least one second protrusion.

3. The connector cap of claim 2 wherein at least one of:
said at least one first protrusion comprises a first slope surface and a first vertical surface; or
said at least one second protrusion comprises a second slope surface and a second vertical surface.

4. The connector cap of claim 2 wherein:
said at least one first protrusion comprises a first vertical surface essentially perpendicular to said outer surface of said first top wall and a first slope surface at an acute angle to said outer surface of said first top wall, and
said at least one second protrusion comprises a second vertical surface essentially perpendicular to said inner surface of said second top wall and a second slope surface at an acute angle to said inner surface of said second top wall.

5. The connector cap of claim 2 wherein:
said inner housing comprises an inner housing retaining feature, and
said outer housing comprises an outer housing retaining feature,
said inner housing retaining feature and said outer housing retaining feature are configured to engage to secure said outer housing on said inner housing and allow rotational movement of said outer housing with respect to said inner housing when said first portion of said safety interface and said second portion of said safety interface are not engaged.

6. The connector cap of claim 5 wherein:
said inner housing retaining feature comprises a first latching protrusion on said outer surface of said first top wall of said inner housing, and
said outer housing retaining feature comprises a second latching protrusion on said inner surface of said second top wall of said outer housing,
said first latching protrusion and said second latching protrusion are configured to latch to secure said outer housing on said inner housing.

7. The connector cap of claim 1 wherein:
said inner housing comprises an inner housing retaining feature, and
said outer housing comprises an outer housing retaining feature,
said inner housing retaining feature and said outer housing retaining feature are configured to engage to secure said outer housing on said inner housing and allow rotational movement of said outer housing with respect to said inner housing when said first portion of said safety interface and said second portion of said safety interface are not engaged.

8. The connector cap of claim 7 wherein:
said inner housing retaining feature comprises a protrusion on an outer surface of said first sidewall of said inner housing, and
said outer housing retaining feature comprises a recess in an inner surface of said second sidewall of said outer housing,
said protrusion and said recess are configured to engage to secure said outer housing on said inner housing.

9. The connector cap of claim 7 wherein:
said inner housing retaining feature comprises a first latching protrusion on said outer surface of said first top wall of said inner housing, and
said outer housing retaining feature comprises a second latching protrusion on said inner surface of said second top wall of said outer housing,
said first latching protrusion and said second latching protrusion are configured to latch to secure said outer housing on said inner housing.

10. The connector cap of claim 1 wherein said second top wall of said outer housing comprises at least one opening extending through said second top wall allowing air to pass through said outer housing.

11. The connector cap of claim 10, wherein said inner housing and said outer housing are configured to allow said air passing through said at least one opening to pass between an inner surface of said outer housing and an outer surface of said inner housing.

12. The connector cap of claim 1, wherein application of a rotational force to said outer housing causes
said rotational movement of said outer housing, and
said second portion of said safety interface to engage said first portion of said safety interface to transfer said rotational movement of said outer housing to said rotational movement of said inner housing to threadably rotate said inner housing to interlock said at least one cap thread with said mating feature of said hub of said needleless connector.

13. The connector cap of claim 12, wherein application of an axial force to said outer housing in a direction of said inner housing facilitates said second portion of said safety interface to engage said first portion of said safety interface.

14. The connector cap of claim 1, wherein
continuous application of an axial force to said outer housing in a direction of said inner housing causes said second portion of said safety interface to engage said first portion of said safety interface in an interference fit, and
application of a rotational force to said outer housing causes
said rotational movement of said outer housing, and
said second portion of said safety interface to continue to engage said first portion of said safety interface to transfer said rotational movement of said outer housing to said rotational movement of said inner housing to threadably rotate said inner housing to remove said at least one cap thread from said mating feature of said hub of said needleless connector.

15. The connector cap of claim 1, wherein at least one of a major diameter, a minor diameter, a pitch, a thread section profile, and a number of threads of said at least one cap thread does not correspond to said mating feature of said hub.

16. The connector cap of claim 1, wherein said at least one cap thread on said inner sidewall surface of said first sidewall comprises a protrusion formed on at least a portion of said at least one cap thread to facilitate said interlocking with said mating feature of said hub of said needleless connector.

17. The connector cap of claim 1, wherein at least a portion of said at least one cap thread comprises a non-engaging portion that does not engage said mating feature of said hub of said needleless connector.

18. The connector cap of claim 1, wherein said at least one cap thread comprises:
at least one interlocking portion formed on a least a portion of said at least one cap thread to facilitate said interlocking with said mating feature of said needleless connector; and
at least one non-engaging portion that does not engage said mating feature of said hub of said needleless connector.

* * * * *